United States Patent [19]

Bucaro

[11] Patent Number: 4,862,899
[45] Date of Patent: Sep. 5, 1989

[54] KIT FOR HOME USE DETECTION OF CERVICAL AND VAGINAL CANCER

[76] Inventor: Russell J. Bucaro, 4007 South Tamarack Trail, Crystal Lake, Ill. 60014

[21] Appl. No.: 170,662

[22] Filed: Feb. 29, 1988

Related U.S. Application Data

[60] Continuation of Ser. No. 914,441, Oct. 2, 1986, abandoned, which is a division of Ser. No. 731,321, May 2, 1985, Pat. No. 4,633,886.

[51] Int. Cl.⁴ .............................................. A61B 10/00
[52] U.S. Cl. ...................................... 128/749; 128/759
[58] Field of Search .............. 128/749, 759, 752, 636; 604/1, 2, 3, 23

[56] References Cited

U.S. PATENT DOCUMENTS

| | | | |
|---|---|---|---|
| 2,664,879 | 1/1954 | Hardy | 128/636 |
| 3,449,080 | 6/1969 | Edwards | 128/636 X |
| 3,877,464 | 4/1975 | Vermes | 604/1 X |
| 3,890,204 | 6/1975 | Avery | 128/759 X |
| 3,913,563 | 10/1975 | Moore et al. | 604/1 X |
| 4,014,746 | 3/1977 | Greenspan | 604/1 X |
| 4,376,634 | 3/1983 | Prior et al. | 128/759 X |
| 4,387,725 | 6/1983 | Mull | 128/759 |

Primary Examiner—Max Hindenburg
Assistant Examiner—John P. Lacyk
Attorney, Agent, or Firm—Frijouf, Rust & Pyle

[57] ABSTRACT

A device is disclosed for home use detection of cervical and vaginal carcinoma. The device comprises a probe of various designs including an aspiration device or a swab for removing cells from the vagina or cervix. The probe is encased to provide a sterile environment. The device includes a container having a rupturable membrane for maintaining a solution in a sterile environment prior to breaking of the rupturable membrane. The rupturable membrane is established for being severed by the probe enabling the probe containing the removed cell to be immersed in the solution in the container. In one embodiment, the container contains a fixing solution for reacting with the cells on the probe enabling the transfer of the sample cells to a testing laboratory. In another embodiment of the invention, the container contains an iodine solution for reacting with the sample cells. The color of the stained sample cells is then compared to a color chart for providing an immediate indication of the test results.

3 Claims, 3 Drawing Sheets

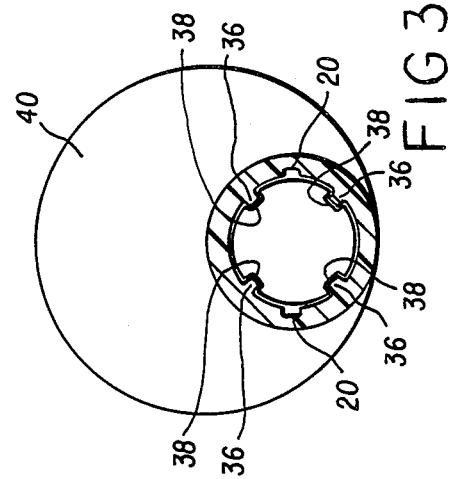
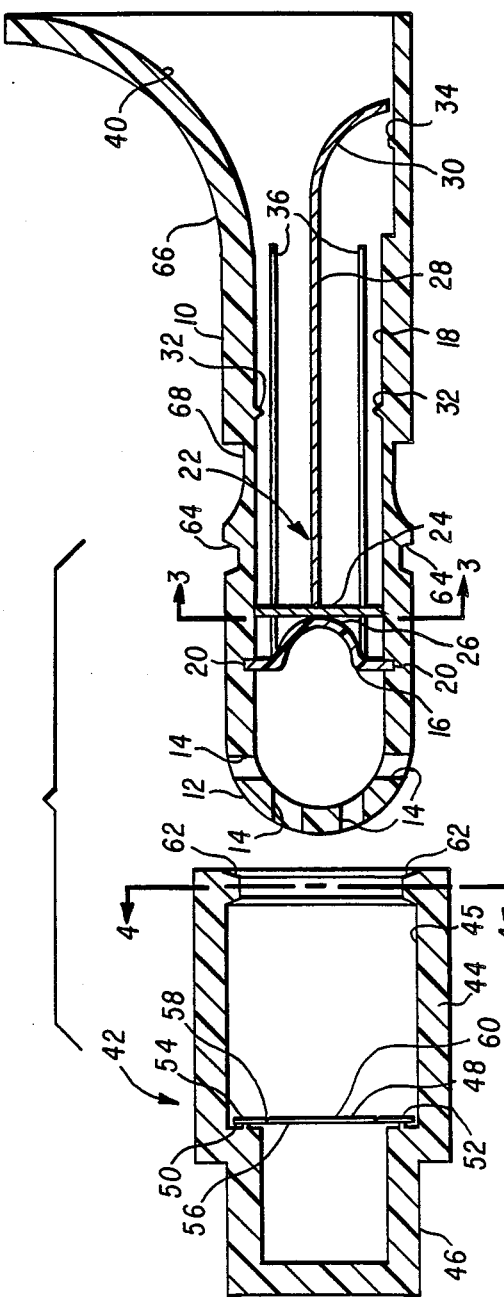
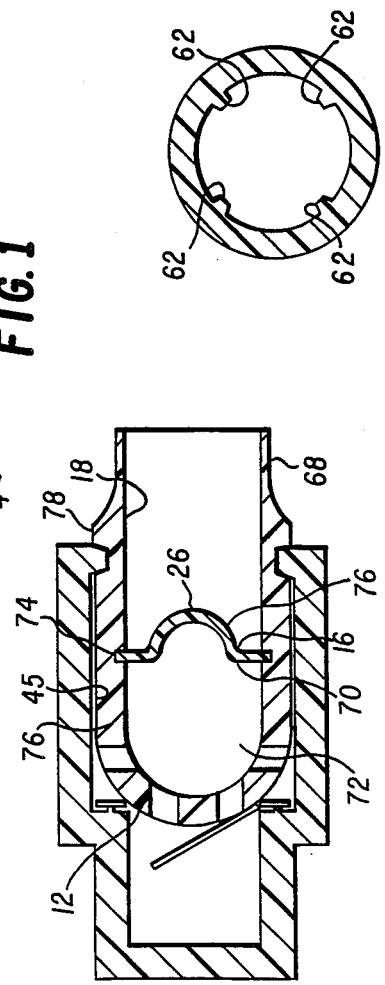

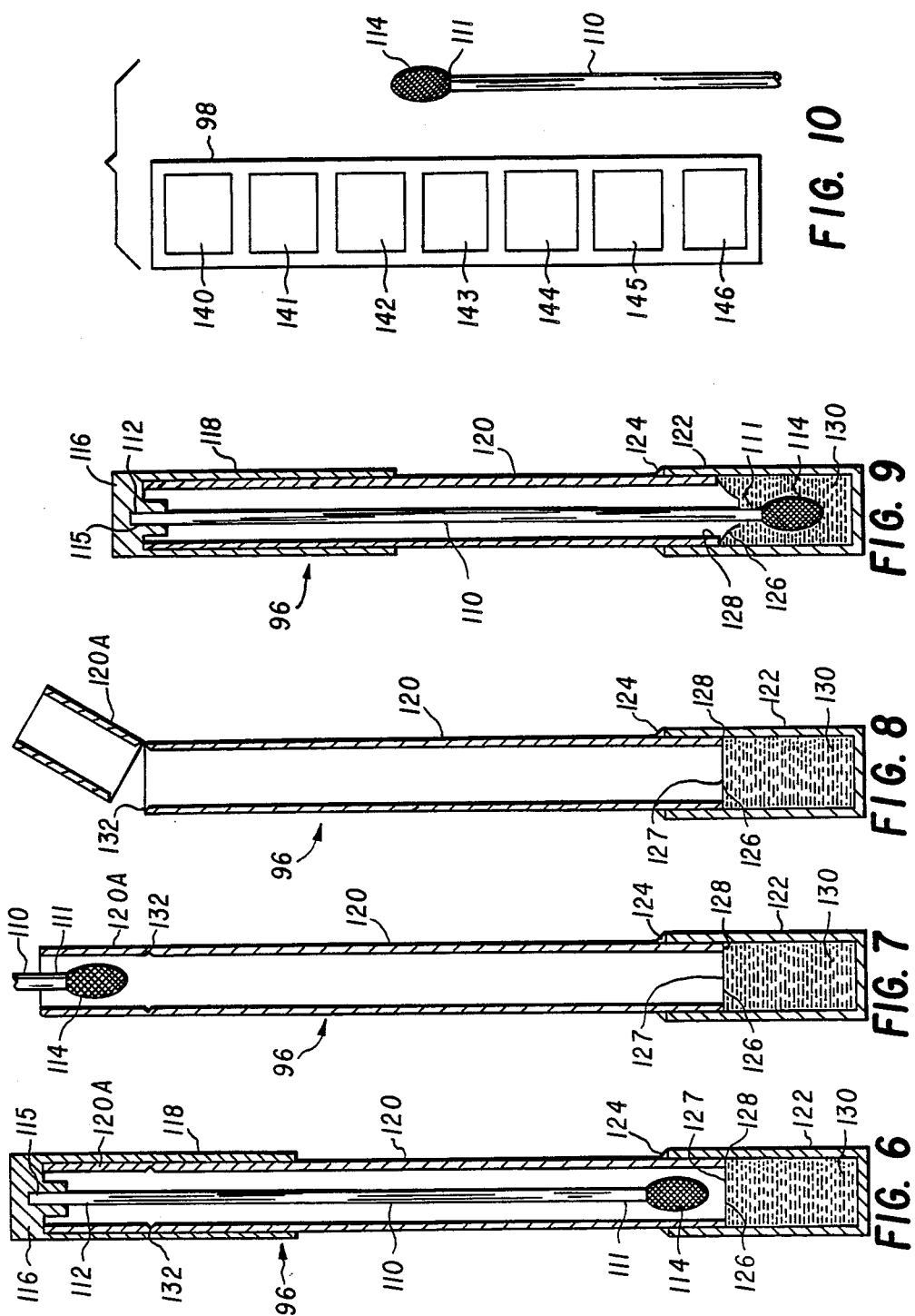

KIT FOR HOME USE DETECTION OF CERVICAL AND VAGINAL CANCER

This application is a continuation; of application Ser. No. 914,441, filed Oct. 2, 1986, which is incorporated by reference as if fully set forth herein, abandoned which is a division of application Ser. No. 731,321 filed May 2, 1985 which is now U.S. Pat. No. 4,633,886.

BACKGROUND OF THE INVENTION

1. Field of the Invention

This invention relates to a device for home use detection of cervical and vaginal carcinoma and the like.

2. Description of the Prior Art

Statistics indicate that a large number of women die each year as a result of cervical cancer.

Gynecologists generally agree that a great proportion of these fatalities could have been avoided if the cervical cancer had been diagnosed earlier. In an ideal situation, women would receive a medical check at short intervals so that the existence of cervical and vaginal carcinoma could be readily diagnosed at an early stage of development and remedial action could be taken before the disease reached a critical stage. All too often the existence of abnormal squamous cells is detected at a stage where the only remedial action is a hysterectomy or removal of all or part of the uterus. Even with the provision of a hysterectomy, surgeons have often found that because of the delay in detecting the infection, the operation has not proved successful in halting the progress of this dreaded disease.

There are a number of factors which deter women from frequent medical tests for cervical and vaginal carcinoma. Firstly, the cost involved in providing medical personnel for carrying out an internal examination has escalated over recent years. Therefore, if a woman is to be examined even once every month, the financial burden imposed upon her often becomes prohibitive. Secondly, a certain degree of embarassment is experienced by most women as they undergo such an internal examination. This embarassment is often magnified in view of the existence of relatively few female gynecologists. Thirdly, the time required by a woman to attend a diagnostic clinic often results in a serious problem, particularly if such visits are to be on a frequent basis. In such cases, the woman, if employed, must require considerable time away from the job. Alternatively, the woman may have young children, and if she is to attend a clinic, it becomes necessary for her to engage the services of a babysitter.

In order to overcome the aforementioned problems, a home use detection device for the detection of cervical and vaginal carcinoma offers many attractive advantages. By the provision of a low cost home use device, a woman is able to carry out such a test at least once a month if not several times a month. The present invention contemplates two embodiments of testing wherein the first embodiment requires the test cells to be forwarded by mail or the like to a testing laboratory whereas the second embodiment enables the cells to be immediately testing in the home. In either embodiment, the woman is released from the embarassment from undergoing an internal examination by a medical practitioner. Not only is the woman permitted to carry out the test in the privacy of her own home, but also, she saves herself the high cost of a medical examination and the other various problems associated with such visits to a medical practitioner such as the arrangements needed to care for her children during such visits.

With regard to the actual requirements for the successful diagnosis of cervical and/or vaginal carcinoma, a sample of cervical or vaginal epithelium is taken by the woman herself. Such epithelium is cellular tissue that covers the surfaces and lines the internal walls of the vaginal cavity. In the first embodiment, the epithelium sample is mixed with a fixing solution and is mailed to a pathological laboratory. At the laboratory, the epithelium sample has added thereto an iodine stain which indicates the existence of normal squamous cell epithelium because normal squamous cell epithelium contains glycogen. The iodine stain reacts with the glycogen to provide a visual indication of normal squamous cell epithelium. However, in the case of abnormal squamous cell epithelium, such epitheliums exhibits pathological activity and is thought to contain little or no glycogen. In view of this lack of glycogen, an abnormal sample of epithelium will not demonstrate the same visual indication when iodine stain is added to the same, thus indicating the existence of squamous cell carcinoma. Since squamous cell carcinoma is thought to comprise over 90% of all cervical carcinomas, this method of cancer detection is very desirable.

In the second embodiment, a sample of cervical or vaginal epithelium is again taken by the woman. The epithelium sample is then mixed with an iodine stain which indicates the existence of normal squamous cell epithelium upon the reaction of the iodine stain with the glycogen. Abnormal sample cells contain little or no glycogen and will not react with the iodine stain. Accordingly, in the second embodiment, a color comparison chart is provided to enable the woman to compare the color of the sample cells treated with the iodine stain with the color comparison chart to indicate the existence of abnormal cells.

Various prior art devices have been proposed for carrying out home use detection of abnormal conditions in the function of the human body. Among such prior art devices can be listed equipment for home use detection of blood pressure and home use testing for pregnancy. More particularly, pap smear kits are known in which the kit includes a cotton wool swab for taking up an epithelium sample and a mailing folder for mailing the sample to a cytology laboratory for diagnosis. In the United States alone, seventy million such pap smears are collected each year and are tested for diagnosis of cancer. However, in the majority of such cases, these pap smears are obtained by skilled medical personnel and not by the patient herself. Therefore, it is the primary object of this invention to provide a device for home use detection of cervical and vaginal carcinoma and the like.

Therefore, an object of this invention is the provision of a low cost home use device for obtaining a sample of squamous cell epithelium.

Another object of the present invention is the provision of a device which is convenient to use by a woman to obtain from herself a sample of squamous cell epithelium.

Another object of this invention is the provision of a device which overcomes the problems associated with frequent visits to a medical clinic for internal examinations.

Another object of this invention is the provision of a home use device wherein the testing and the results thereof may be obtained at the home of the user.

Another object of this invention is the provision of a home use device which is easily able to be sent by mail to a pathological laboratory, or more particularly, a cytology laboratory as the cytology laboratory specialized in diagnosis of pap smears.

Another object of the invention is the provision of a tube having a rounded end for insertion within the vagina. A flexible diaphragm cooperates with a plunger for aspirating a sample of squamous epithelium from the vagina into the elongated tube. A fixing container having a rupturable membrane and containing a fixing solution forms a sealing engagement upon insertion of the elongated tube into the cylindrical portion to rupture the membrane and mix the fixing solution with the squamous epithelium from the vagina.

Another object of this invention is the provision of a probe for removing a sample of squamous epithelium from the vagina or cervix. A staining container having a rupturable membrane and containing an iodine stain solution enables the cells present on the probe to be mixed with the iodine stain. The color of the treated cells is then compared to a color comparison chart accompanying the test kit.

The foregoing has outlined some of the more pertinent objects of the present invention. These objects should be construed as being merely illustrative of some of the more prominent features and applications of the invention. Many other beneficial results can be attained by applying the disclosed invention in a different manner or modifying the invention within the scope of the disclosure. Particularly with regard to the use of the invention disclosed herein, this should not be construed as limited to a device for home use detection of cervical and vaginal carcinoma, but should include a disposable device for home use detection of any abnormal condition of the squamous cell epithelium of the vaginal or cervical region.

SUMMARY OF THE INVENTION

The detection device of the present invention is defined by the appended claims with a specific embodiment shown in the attached drawing. A device is disclosed for home use detection of cervical and vaginal carcinoma. The device comprises a probe of various designs including an aspiration device or a swab for removing cells from the vagina or cervix. The probe is encased to provide a sterile environment. The device includes a container having a rupturable membrane for maintaining a solution in a sterile environment prior to breaking of the rupturable membrane. The rupturable membrane is established for being severed by the probe enabling the probe containing the removed cells to be immersed in the solution in the container. In a first embodiment, the container contains a fixing solution for reacting with the cells on the probe enabling the transfer of the sample cells to a testing laboratory. In a second embodiment of the invention, the container contains an iodine solution for reacting with the sample cells. The color of the stained sample cells is then compared to a color chart for providing an immediate indication of the test results.

In the first embodiment of the invention, the container having a rupturable membrane maintains a fixing solution therein in a sterile condition prior to the breaking of the rupturable membrane. The rupturable membrane is established for being severed by the probe enabling the probe containing the removed cells to be immersed in the fixing solution in a sterile condition. The container and the probe are established to provide a sealing engagement therebetween enabling the removed vaginal cells immersed in the fixing solution to be forwarded to the test laboratory for further analysis.

In the second embodiment of the invention, the container having a rupturable membrane maintains an iodine stain in a sterile condition prior to breaking the rupturable membrane. The rupturable membrane is established to be severed by the probe enabling the probe containing the removed cells to be immersed in the iodine stain in a sterile condition. A comparison chart comprising a plurality of colors is provided for comparing the extent of stain by the iodine of the cells present on the probe to enable the consumer to determine the presence of abnormal sample cells. In either the first or second embodiments of the invention, a probe may comprise a semi-rigid member with a swab disposed at the distal end thereof or in the alternative, may comprise an aspirator device for removing cells from the consumer. Various other probe devices may likewise be used for this invention.

The foregoing has outlined rather broadly the more pertinent and important features of the present invention in order that the detailed description of the invention that follows may be better understood so that the present contribution to the art can be more fully appreciated. Additionally, features of the invention will be described hereinafter which form the subject of the claims of the invention. It should be appreciated by those skilled in the art that the conception of a specific embodiment disclosed may be readily utilized as a basis for modifying or designing other devices for carrying out the same purposes as the same invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and the objects of the invention, reference should be had to the following description taken in conjunction with the accompanying drawings in which:

FIG. 1 is a side view in section of a first embodiment of a home use detection device of the present invention;

FIG. 2 is a side view in section of the device shown in FIG. 1 with the rounded head, flexible diaphragm and a portion of the elongated tube inserted within the fixing container;

FIG. 3 is a cross-sectional view taken on the line 3—3 of FIG. 1;

FIG. 4 is a cross-sectional view taken on the line 4—4 of FIG. 1;

FIG. 6 is a sectional view of the second embodiment removed from the consumer package;

FIG. 7 is a sectional view of the second embodiment showing the removal of a probe;

FIG. 8 is a sectional view of the second embodiment illustrating the severing of a portion of the device;

FIG. 9 is a sectional view of the second embodiment of the invention showing the staining of sample cells; and FIG. 10 is a plan view of the second embodiment illustrating the comparison of the stained cells to a color chart.

DETAILED DESCRIPTION

Figure 5:
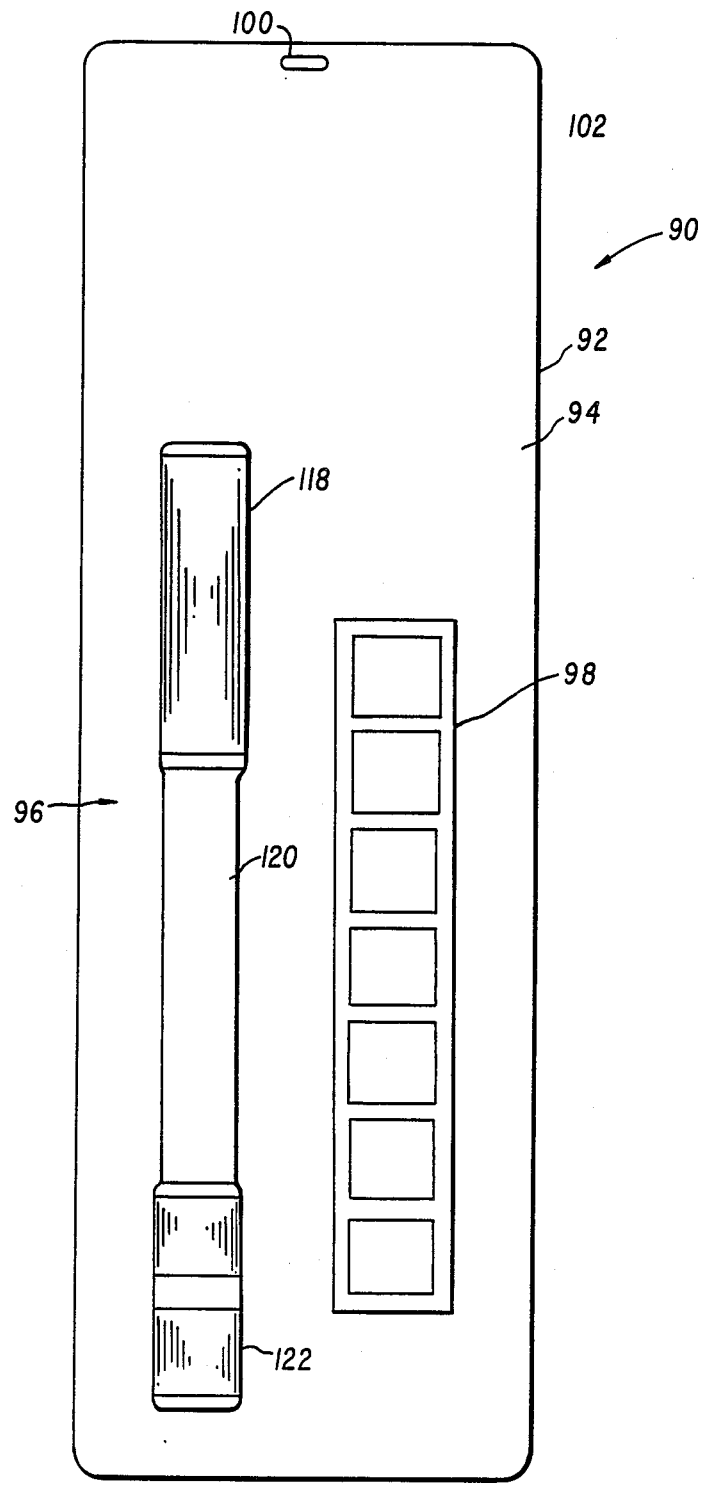
FIG. 5 is a plan view of a second embodiment for a home use detection device of the present invention in a consumer package.

FIG. 1 is a side view in section of a first embodiment home use device for the detection of cervical or vaginal carcinoma. The device includes a probe shown as an elongated tube 10 having at one end thereof a rounded end 12 defining a plurality of orifice 14. A flexible diaphragm 16 is disposed within the elongated tube 10 and is secured to the internal wall 18 of the elongated tube 10 by means of diametrically opposed recesses 20. A plunger, generally designated 22 is disposed within the elongated tube 10 and is axially moveable relative to the elongated tube 10. The plunger 22 includes a piston 24 which is releasably secured to a central bulbous portion 26 of the flexible diaphragm 16. The piston 24 is connected to a piston rod 28 having a trigger 30. Axial movement of the piston 24 relative to the elongated tube 10 is limited by internally projecting stops 32 and 34 which project inwardly from the internal wall 18 of the elongated tube 10. A first set of stops 32 limits movement of the piston away from the rounded end 12 of the elongated tube 10 while a second set of stops 34 limits movement of the piston 24 towards the rounded end 12. Internally projecting longitudinally extending splines 36 extend from and are integral with the internal wall 18 of the elongated tube 10. The splines 36 cooperate with longitudinally extending grooves 38 defined by the piston 24 to guide the piston 24 along the internal wall 18 of the elongated tube 10 as shown in FIG.. 3. The splines 36 and cooperating grooves 38 function to prevent relative rotation between the piston 24 and the elongated tube 10 which could sever the connection between the piston 24 and the bulbous portion 26. Additionally, the splines 36 and grooves 38 locate the trigger 30 relative to the second set of stops 34. A shield 40 is disposed integrally with the elongated tube 10 at the end of the elongated tube 10 remote from the rounded end 12. The integral shield 40 serves the purpose of limiting the distance to which the rounded end 12 and elongated tube 10 is able to penetrate into the vagina.

A fixing container generally designated 42 includes a cylindrical portion 44 having an internal diameter 45 substantially the same as the external diameter of the elongated tube 10 to create a sealing engagement therebetween as shown in FIG. 2. The fixing container 42 further includes an ampoule 46 and a rupturable membrane 48 disposed between the ampoule 46 and the cylindrical portion 44. The ampoule 46 may be of a cup shaped configuration having a rim 50. The rim 50 includes an annular upstanding ridge 52 to which the peripheral edge 54 of the membrane 48 is sonically welded. The membrane 48 has a first side 56 which is in contact at the peripheral edge 54 with the ridge 52. An annular portion 58 of the membrane 48 is of reduced thickness to facilitate the rupture of the membrane 48 when the rounded end 12 of the elongated tube 10 is inserted into the cylindrical portion 44 and against the second side 60 of the membrane 48.

Inwardly projecting ears 62, disposed at the distal end of the cylindrical portion 44 cooperate with an annular groove 64 defined by the external wall 66 of the elongated tube 10 such that when the rounded end 12 is inserted within the cylindrical portion 44, the inwardly projecting ears 62 snap into locking engagement with the annular groove 64 while the forward end of the rounded end 12 presses against the second side 60 of the membrane 48 and ruptures the same by virtue of the reduced thickness of the annular portion 58. A fluid tight seal is created between the internal diameter 45 and the cylindrical portion 44 and the external diameter of the elongated tube 10.

With the membrane 48 ruptured, the fixing solution contained within the ampoule 46 is permitted to flow through the plurality of orifice 14 and mix with the squamous cell epithelium contained within the elongated tube 10 and fix the same.

The external wall 66 of the elongated tube 10 is provided with a weakened section 68 located at a greater distance from the rounded end 12 than the distance of the annular groove 64 from the rounded end 12. The weakened section 68 is provided to permit the breaking away of a portion of the elongated tube 10 and integral shield 40 and plunger from the rounded end 12, diaphragm 16 and a portion of the elongated tube 10 within the fixing container 42. The broken off portion containing the fixed sample of squamous cell epithelium as shown in FIG. 2 can then be placed within a mailing envelope for dispatch to the pathological laboratory.

As shown more particularly in FIG. 2, the flexible diaphragm 16 includes a first side 70 which together with the rounded end 12 and a portion of the elongated tube 10, defines a cavity 72 for the reception of aspirated squamous cell epithelium. The flexible diaphragm 16 is secured adjacent the internal wall 18 of the elongated tube 10 along the peripheral edge 74 of the diaphragm. A second side 76 of the diaphragm 16 is releasably secured to the piston 24 in the region of the bulbous portion 26. In this manner, the elongated tube 10 is divided by the flexible diaphragm 16 into a first portion 78 which in part defines the cavity 72 and a second portion 80 which bonuses the plunger 22.

In use of the detection device, the rounded end 12 of the elongated tube 10 is inserted within the vagina and penetrates the vaginal canal as far as permitted by the integral shield 40. At this location, the rounded end 12 is disposed in the region of the cervix. The plunger 22 is reciprocated within the elongated tube 10 by manipulation of the trigger 30 which is an extension of the piston rod 28. Axial movement of the piston rod 28 results in reciprocation of the piston 24 and the releasably secured bulbous portion 26 of the flexible diaphragm 16. Reciprocation of the flexible diaphragm 16 aspirates squamous cell epithelium from the cervical; region through the plurality of orifice 14 into the cavity 72. Having taken an epithelium sample as described herein before, the elongated tube 10 is removed from the vagina and the rounded end 12 is inserted into the cylindrical portion 44 of the fixing container 42 until the inwardly projecting ears 62 lockably engage the annular grooves 64 disposed around the external wall 66 of the elongated tube 10 thus creating a seal between the internal diameter 45 and the external diameter of the elongated tube 10 At this location within the cylindrical portion 44, the rounded end 12 presses against the second side 60 of the membrane and ruptures the same about the annular portion 58 of the rupturable membrane due to the reduced thickness of the annular portion 58. With the membrane ruptured, the fixing solution contained within the ampoule 46 flows through the plurality of orifice 14 to mix with the squamous cell epithelium to stabilize the cells within the cavity 72. The shield 40 and plunger 22 housed within a portion of the elongated tube 10 are then removed from the fixing container 42, rounded end 12 and diaphragm 16 by breaking the elongated tube 10 about the weakened section 68. The fixing container 42 and fixed epithelium sample contained within the cavity 72 are then inserted into a mailing folder for dispatch to a cytological laboratory for diagnosis of the enclosed sample.

The device of the present invention may be of any suitable material but preferably the elongated tube 10 and fixing container 42 are of plastic material and the flexible diaphragm is of a rubber or plastic material.

FIGS. 5–10 illustrate a second embodiment of the invention shown as a home cancer kit 90 comprising a semi-rigid board such as cardboard 92 and an overlapping plastic material such as a shrink wrap or the like or blister pack for covering a testing instrument 96 and a color chart 98 in an untampered condition. An aperture 100 may be utilized for suspending the kit 90 in a display rack. Appropriate trademarks and descriptive terms such as 102 may be printed on the board with appropriate instructions on the reverse side of the board 92 (not shown).

The device 96 shown in more detail in FIGS. 6–10 comprises a probe 110 shown as a semi-rigid member such as tubular plastic and the like containing a swab 114 affixed to a first end 111 of member 110. The swab is preferably chemically treated or of a material which is impervious to an iodine stain whereby the swab material is not discolored by insertion within an iodine stain solution. This ensures that the only color present on the swab 114 will be the staining of cells.

The second end 112 of the semi-rigid member 110 is received within an aperture 115 of a base 116 of a tubular cap 118. A tubular end cap 118 is preferably made of a plastic material which may receive the second end 112 of the semi-rigid member 110 by a press-fit or suitable adhesive fastening.

A body member 120 is shown as a tubular plastic member which receives an ampoule end cap 122 which forms a sealing engagement with the body member 120 by a suitable fastening such as sonic welding or adhesive, for example, at 124. The ampoule end cap 122 includes a rupturable membrane 126 which is shown in the embodiment affixed by sonic welding, adhesive or the like, to the an 128 of body member 120. Although the rupturable membrane 126 has been shown secured to the end 128 of body member 120, it should be appreciated by those skilled in the art that numerous other positions and affixing means may be utilized with the present invention. The ampoule defined by the ampoule end 122 and the rupturable membrane 126 maintains an iodine stain 130 in a sterile condition prior to use. The body member 120 includes a weakened region 132 in the wall thereof for severing a frangible portion 120A from body member 120 as well be described in greater detail hereinafter.

FIG. 6 illustrates the device 96 immediately after removal from the consumer package 90 as shown in FIG. 5.

FIG. 7 illustrates the removal of the end cap 118 and the associated semi-rigid member 110 and the swab 114 for inserting the swab 114 into the vaginal canal to collect specimen cells.

Thereafter, the frangible portion 120A of the body member 120 is removed by breaking by the consumer as shown in FIG. 8 enabling the semi-rigid member 110 and the swab 114 to be inserted in the body member 120 as shown in FIG. 9. Since the frangible portion 120A of body member 120 has been removed, the complete insertion of the end cap 118 on body member 120 enables the swab 114 to sever membrane 126 and immerse the swab 114 into the iodine stain 130. This process ensures that the outer portion 127 of the membrane 126 non-contacting the iodine stain is maintained in a sterile condition along with the swab 114, the semi-rigid member 110 and the like.

After proper staining by the iodine stain 130, the end cap 118 and semi-rigid member 110 is again withdrawn from body member 120 and the swab 114 is compared to the color chart 98 as shown in FIG., 10. A color chart 98 comprises a plurality of colors 140–146 for comparison with the color of the stained cells on the swab 114. If the cells are normal, the normal cells with combine with the iodine and produce an iodine stained sample. However, if the cells are abnormal, the iodine stain will not react with the sample cells and non-iodine stained specimen will be present. By comparing the actual color of the cells on swab 114 with the color charts specifically color blocks 140–146, the presence of abnormal cells may be detected by the consumer.

The foregoing has disclosed a novel device in a first and a second embodiment for the home detection of cervical or vaginal cancer. It should be appreciated that although two probes have been disclosed for the present invention, numerous other probes may be utilized and the probes may be interchanged within the two different embodiments as should be well known to those skilled in the art.

A device for home use detection of cervical and vaginal carcinoma as herinbefore described provides a low cost means for a woman to regularly take epithelium samples in the privacy of her own home. The device additionally provides a reduction in the demands placed upon medical personnel who already are faced with enormous work load problems.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the construction and arrangements of parts may be resorted to without departing from the spirit and scope of the invention.

What is claimed is:

1. A kit for the home detection of squamous cell carcinoma of the cervix and vagina comprising:
   a probe including a semi-rigid member;
   said semi-rigid member having a proximal end and a distal end with a swab at said distal end of said semi-rigid member for collecting and removing cells in use from the vagina and cervix;
   means for encasing said probe in a sterile environment prior to use;
   a container;
   a weakened region formed on said container defining a frangible portion and a body portion and for enabling said frangible portion to be severed from said body portion;
   said body portion having a rupturable membrane for maintaining an iodine stain in a sterile environment prior to the breaking of said rupturable membrane;
   said swab being configured such that said swab is able to rupture said rupturable membrane of said body portion to permit said swab to be immersed into said iodine stain when said swab is positioned within said container;

said frangible portion of said container being severable from said body portion of said container to enable said swab to reach and to break said rupturable membrane of said body portion thereby permitting said swab to be immersed into said iodine stain; and a comparison chart comprising a plurality of colors for comparing the extend of stain by the iodine of the cells present on said swab to enable the consumer to determine the presence of squamous cell carcinoma.

2. The kit as set forth in claim 1 including sterile means for maintaining a sterile condition on said rupturable membrane.

3. The kit set forth in claim 1 including limiting means for limiting the penetration of said probe into the vagina.

* * * * *